United States Patent [19]
Cuthbert et al.

[11] 3,944,369
[45] Mar. 16, 1976

[54] OPTICAL COMPARATOR SYSTEM TO SEPARATE UNACCEPTABLE DEFECTS FROM ACCEPTABLE EDGE ABERRATIONS

[75] Inventors: John David Cuthbert, Bethlehem; Delmer Lee Fehrs, Easton; David Farnham Munro, Alburtis, all of Pa.

[73] Assignee: Bell Telephone Laboratories, Incorporated, Murray Hill, N.J.

[22] Filed: May 24, 1974

[21] Appl. No.: 473,233

[52] U.S. Cl. .............................. 356/167; 356/168
[51] Int. Cl.² .......................................... G01B 11/24
[58] Field of Search ............. 356/156, 167, 168, 71; 178/6

[56] References Cited
UNITED STATES PATENTS
3,753,617  8/1973  Ehrat .............................. 356/167 X FOREIGN PATENTS OR APPLICATIONS
1,944,631  5/1970  Germany ............................ 356/167

*Primary Examiner*—Alfred E. Smith
*Assistant Examiner*—Richard A. Rosenberger
*Attorney, Agent, or Firm*—C. S. Phelan

[57] ABSTRACT

In an optical comparison inspection system a single beam from a scanning light source is split to produce a pair of synchronously scanning focused light beams. One of the beams is directed onto a reference, light affecting patterned workpiece and the other beam is directed onto a similar patterned workpiece to be inspected. Both workpieces are mounted in optically equivalent positions on a traverse table which has a direction of travel orthogonal to parallel planes containing the scanning light beams. Pattern differences are represented by differences in photodetected representations of the two light beams, which are intensity modulated by the patterned workpieces. By electronically gating preselected combinations of the two modulated signals with circuitry employing multiple threshold detection elements, a resultant signal is produced which enables allowable edge aberrations to be discriminated from unacceptable defects in the patterns. Suitable display of the resultant signal permits an operator to rapidly ascertain both the number and location of only unacceptable defects.

22 Claims, 7 Drawing Figures

(a) PATTERN WITH DEFECTS AND EDGE ABERRATIONS (b) REFERENCE PATTERN (c) COMPARATIVE DIFFERENCE PATTERN (d) TOLERANCE ZONE WITHIN WHICH EDGE ABERRATIONS ARE ACCEPTABLE (e) SUPERIMPOSED TOLERANCE ZONE AND DIFFERENCE PATTERNS (f) SELECTIVE DIFFERENCE PATTERN SHOWING UNACCEPTABLE DEFECTS

OPTICAL COMPARATOR SYSTEM TO SEPARATE UNACCEPTABLE DEFECTS FROM ACCEPTABLE EDGE ABERRATIONS

BACKGROUND OF THE INVENTION

1. Field of the Invention

This invention relates to optical systems and, in particular, to optical systems used for making selective comparative inspections.

2. Description of the Prior Art

To achieve acceptable circuit yields and high reliability in integrated circuits and thin film circuits presently requires the performance of a visual inspection to verify the integrity of both mask and metallization patterns. Recent design trends toward higher levels of integration in both integrated and film circuits have increased the need for pattern verification. However, the resulting pattern complexity of integrated and film circuits has made visual inspection of both masks and metallization patterns more difficult and more expensive. Typically, an inspector must scan a pattern, detect potentially harmful defects in the mask or metallization patterns and decide which of the detected defects may indeed be critical to circuit performance. Pressures to decrease inspection cost may force inspectors to adopt higher scanning rates, possibly at the expense of reliable defect detection.

Some typical defects which can interfere with the light transmission characteristics of the mask or the electrical properties of the metallization pattern and which can affect final circuit yields are pinholes, protrusions, scratches, and unetched film.

One possible solution to the inspection reliability versus cost problem is automation. However, complete automation of inspection is considered extremely difficult to achieve both technically and economically. The development of more limited automatic techniques, which reliably detect and display all mask defects which might adversely affect the performance of a circuit fabricated by the use of such a mask, is considered much more realistic. Such a semiautomatic scheme would relieve the inspector of the mechanical aspects of inspection and free him to concentrate on the decision function, as to the effects on circuit performance if a detected defect is not corrected provided that an efficient interface is established between the inspector and the inspection machine.

Some semiautomatic optical comparison systems have been described in the literature and are in commercial use. These systems typically utilize at least two synchronously scanning focused light sources to illuminate the patterned masks or workpieces which are placed in optically equivalent positions. A point-by-point comparison of the readings provided by the scanning sources indicates any relative differences between the two patterns. Unfortunately, pattern dimensions vary within some acceptable range from workpiece to workpiece. For some fine line patterns, these dimensional variations result in acceptable pattern aberrations which are of the same approximate size as potentially critical defects. These defects can adversely affect the circuits formed by the use of the inspected masks.

Accordingly, it is one object of the present invention to separate acceptable pattern aberrations from true mask imperfections, the latter being potentially capable of causing failures in circuits fabricated by the use of uninspected masks.

Another object is to achieve a more uniform quality in the circuits fabricated by the use of inspected masks by more accurately and more consistently controlling the decision threshold between acceptable and unacceptable mask patterns.

A further object of the present invention is to reduce the cost of making comparative inspections by decreasing operator interaction with the optical scanning equipment.

SUMMARY OF THE INVENTION

The foregoing and other objects of the invention are realized in an illustrative embodiment wherein first and second synchronously scanning light beams are intensity modulated by the patterns on a test and a reference workpiece. Application of these intensity modulated signals to electronic circuitry which gates preselected combinations of the two modulated signals in accordance with a number of predetermined threshold levels produces a resultant signal which is indicative of any light affecting characteristics in the test workpiece which differ significantly from those in the reference workpiece. By controlling the manner in which the two modulated signals are combined, acceptable pattern aberrations can be advantageously separated from other types of unacceptable pattern variations which produce similar light affecting characteristics. Suitable display of the resulting signal on, for instance, an electrooptical display device permits an operator to rapidly ascertain both the number and the location of only the potentially unacceptable pattern defects.

Accordingly, it is one feature of the present invention that a point-by-point comparison is made to detect relative interpattern differences between a patterned workpiece and a reference workpiece, but those differences associated with minor edge aberrations are ignored while defects in the interior of a pattern are detected.

Another feature is that more consistent enforcement of preselected inspection criteria can be advantageously achieved because of electronically controlled decision thresholds.

A further feature of the present invention is that the processing electronics are inexpensive and can be advantageously retrofitted to many dual beam, comparative scanning optical inspection systems.

Yet another feature is that both the number and the location of the detected defects are readily ascertainable by a visual inspection of an electrooptical display device.

BRIEF DESCRIPTION OF THE DRAWINGS

The aforementioned features and objects of the invention as well as other features and objects will be better understood upon a consideration of the following detailed description and the appended claims in connection with the attached drawings of an illustrative embodiment in which:

DETAILED DESCRIPTION

Figure 1:
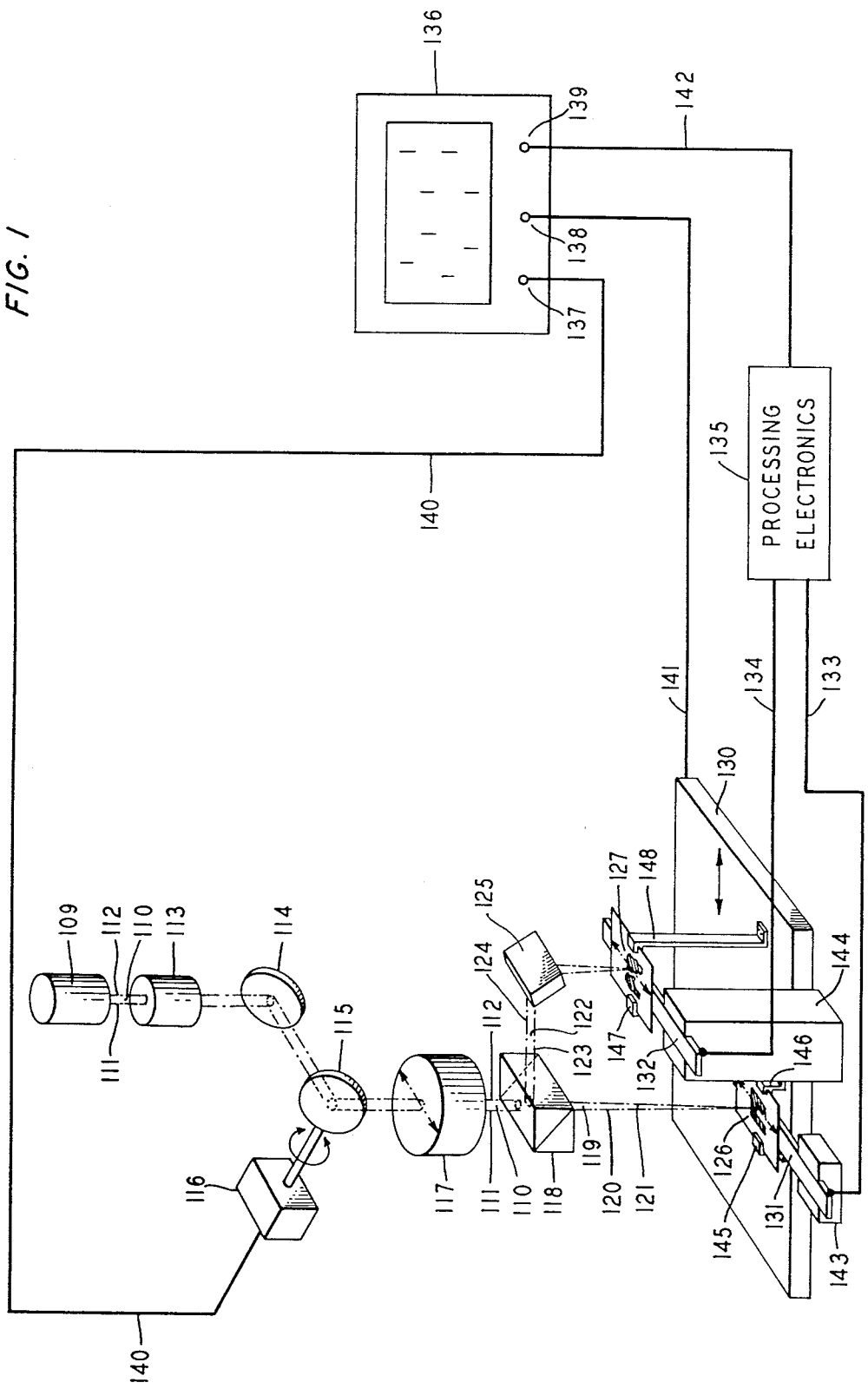
FIG. 1 is a schematic representation of a dual beam optical comparison system.

Operation of the optical comparison system, shown in schematic form in FIG. 1, is most easily understood by separating the description into three parts. Part one will describe the optical portion of the system including visual display aspects. The second part will describe criteria to be used for separating unacceptable pattern variations from acceptable edge aberrations. Since the criteria depend to some extent on a number of light beam characteristics such as beam cross-sectional area or spot size and the distribution of light intensity in the beam, this discussion follows the description of the optical system. Part three of the description will describe a translation of the separation criteria into an electronic implementation thereof. Utilization of this approach should result in a simplification of the overall system description.

1. Optical System

A dual beam optical comparison system is shown in FIG. 1. For such a system to provide a meaningful point-by-point comparison of two objects to be compared it is essential that the two beams have virtually identical characteristics, that the objects be scanned synchronously by the two beams, and that the two objects be in optically equivalent positions. The first and second of these requirements are readily satisfied by the use of a common light source 109 to generate the two scanning beams. In one embodiment of the invention light source 109 is a helium-neon laser having an operating wavelength of 6328 Angstroms. Utilization of a laser as light source 109 provides a parallel output light beam 110, defined by beam edges 111 and 112, the intensity of which is approximately gaussian as a function of distance along a beam radius. Beam edges 111 and 112 are conveniently defined as being at the $1/e^2$ intensity points, where $e$ is the base of a natural logarithm. The approximately gaussian form of light beam 110 ensures that a scanning beam spot also has an approximately gaussian intensity distribution. Care must be taken to minimize aperturing of beam 110, so that diffraction effects which cause departures from the gaussian distribution are minimized. Final spot size is controlled by applying light beam 110 to a beam expander 113 which expands beam 110 to a diameter of about one inch at the $1/e^2$ intensity points, while at the same time collimating individual light rays within the beam to make them parallel to one another. In an alternate embodiment where a laser is not used, an incoherent light source plus suitable collimating optics are substituted for light source 109.

Beam 110, following expansion, is deflected by stationary mirror 114 to a torsionally oscillating mirror 115. The oscillations of mirror 115 impart a scanning motion to beam 110 without altering its intensity or collimation characteristics. These oscillations are about a line parallel to a plane containing either one of the two objects to be compared, reference workpiece 126 or test workpiece 127. Utilization of stationary mirror 114 to deflect beam 110 onto a reflecting face of oscillating mirror 115 permits light source 109 and beam expander 113 to be physically located in a more convenient position in the optical signal path than would otherwise be the case if stationary mirror 114 were excluded. Morever, the use of stationary mirror 114 ensures that beam 110 will be incident at the axis of oscillation of mirror 115 thereby maximizing the length of a scan.

After impingement on oscillating mirror 115, beam 110 is directed to lens 117. Oscillating mirror 115 is located in a back focal plane passing through a focal point of lens 117. In order to achieve a telecentric scan, wherein a central light ray in beam 110 is maintained perpendicular to the planes containing workpieces 126 and 127 throughout a scan, lens 117 must have its entrance pupil outside the body of the lens.

Synchronous scanning of workpieces 126 and 127 is ensured by deriving beams 119 and 122, as defined by pairs of beam edges 120–121 and 123–124, respectively, from the same beam 110. Beam division is effected by applying beam 110 to beam splitter 118 which produces two orthogonal output beams 119 and 122. Beam 122 is redirected by mirror 125 and brought into parallel alignment with beam 119. The optical path lengths traveled by beams 119 and 122, following beam division, must be equal.

The third essential requirement, that the two objects be held in optically equivalent positions, is satisfied when workpieces 126 and 127 are mechanically aligned with one another as they are affixed to traverse table 130 by pairs of mounting clips 145–146 and 147–148, respectively. The alignment tolerance range plus the range on allowable pattern edge variations define a tolerance zone within which edge aberrations are acceptable. Beam spot size at the points of incidence on workpieces 126 and 127 and the minimum sized defects to be detected are used to establish the limits on this tolerance zone.

Beams 119 and 122 are intensity-modulated by the patterns on workpieces 126 and 127 and these intensity variations are detected by reference photodiode 131 and test photodiode 132, respectively, which lie beneath workpieces 126 and 127. Photodiodes 131 and 132 are affixed to support brackets 143 and 144, respectively, with brackets 143 and 144 being fixedly mounted independently of traverse table 130. Photodiodes 131 and 132 are directly in the path of beams 119 and 122, respectively. Leads 133 and 134 couple electrical equivalents of the intensity-modulated light signals to processing electronics 135 about which more will be said in part three of this description.

Where workpieces 126 and 127 have reflective characteristics, the optical equipment following lens 117 in the paths traveled by beams 119 and 122 is slightly modified and photodiodes 131 and 132 are shifted to a location above workpieces 126 and 127.

Complete point-by-point illumination of workpieces 126 and 127 is provided by the back and forth motion of traverse table 130 in a plane which is orthogonal to first and second parallel planes containing light beams 119 and 122 as the beams are scanned back and forth by the oscillations of mirror 115. Electrical signals produced by photodiodes 131 and 132 during the scanning are coupled by leads 133 and 134 to processing electronics 135, to be described, and from there on a lead 142 to an intensity modulation input 139 of a storage oscilloscope 136. Horizontal and vertical deflection of the oscilloscope 136 are controlled by electrical signals from galvanometer oscillator 116 applied on a lead 140 to a horizontal deflection input 137 and by signals derived, by transducers not shown, from the motion of table 130 and supplied on a lead 141 to a vertical deflection input 138. The horizontal and vertical deflection signals provide positional information in a two dimensional display, whereas the signal applied to the intensity modulation input 139 is a binary signal which provides an indication of whether or not an unacceptable pattern defect is present and detected. The long persistence time feature of the storage oscilloscope 136 permits the results of a complete inspection to be displayed simultaneously thereby allowing an operator to mark the location of the defects on test workpiece 127 for subsequent repair purposes. The binary signal can also be advantageously used to activate a counter, thereby providing a count of the number of defects.

2. Edge Aberration Avoidance Criteria

Figure 2:
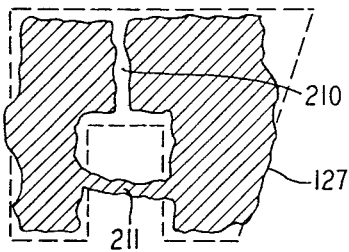
FIG. 2 illustrates unacceptable defects as compared with edge aberrations in a light transmissive workpiece.
Figure 2:
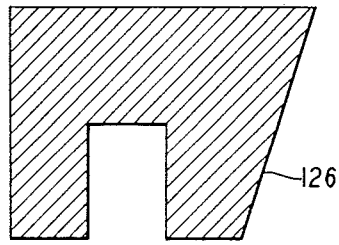
Figure 2:
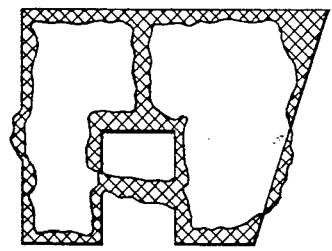
Figure 2:
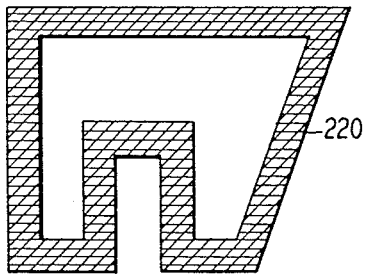
Figure 2:
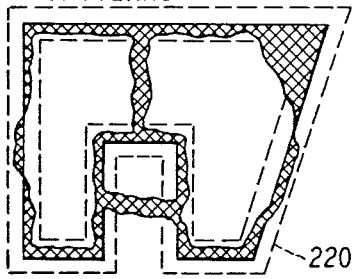
Figure 2:
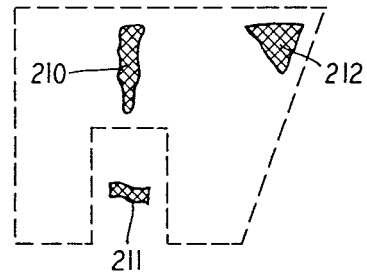

The distinction between edge aberrations and unacceptable pattern defects is more easily understood by considering a typical light transmissive pattern that might be carried by workpieces 126 and 127. A light transmissive pattern on test workpiece 127 and, in idealized form, a light transmissive pattern on reference workpiece 126 are illustrated in FIGS. 2a and 2b, respectively. Those areas which are shaded represent opaque regions of workpieces 126 and 127. These regions greatly attenuate light beams 119 and 122. Unshaded areas represent transparent regions which allow beams 119 and 122 to pass through workpieces 126 and 127 with little or no attenuation. The broken lines shown in FIG. 2a represent the desired pattern outline.

Test workpiece 127 has several unacceptable pattern defects, thereon as well as irregularities around the pattern edges. These irregularities around the pattern edges are usually referred to as edge aberrations. Superimposing reference workpiece 126 on top of test workpiece 127, as shown in FIG. 2c, illustrates those areas, shown shaded, between the two patterns where modulation differences would exist between the output signals from photodiodes 131 and 132. Moderate edge aberrational effects typically are not of such a serious nature as would result in catastrophic failures in circuits fabricated by the use of such a workpiece. However, the pattern defects 210 through 212, shown shaded in FIG. 2f, very frequently do cause such failures. For example, a break 210 as shown in FIG. 2a, separates the two major regions of the pattern on workpiece 127. This break could result in an open circuit condition. While the circuit effects resulting from defects drastically differ from those of edge aberrations, the difference in modulation level between the signals delivered by photodiodes 131 and 132, caused by the two different phenomena are not readily discernible.

To separate edge aberrational effects, a tolerance zone 220 which places specified limits on the amount of variations in edge aberrations which will be acceptable is selected in accordance with beam spot size and minimum sized defects to be detected. This tolerance zone 220 is shown in FIG. 2d. Details regarding the physical implementation of this zone will be discussed in part three. In FIG. 2e, superposition of FIG. 2d on top of FIG. 2c illustrates those edge aberrations which fall within the tolerance zone, shown by broken lines, and hence are separable. Subtraction of the edge aberrational effects from the total comparative pattern differences yields those areas in test workpiece 127 which constitute unacceptable pattern defects 210 through 212. These defects are shown shaded in FIG. 2f.

It should be noted that the focused spot size of beams 119 and 122 at the planes containing workpieces 126 and 127 must be at least the same order of magnitude as the defects to be detected and typically, the spot size is as small as the smallest defect to be detected. It should also be noted that reference workpiece 126, as illustrated in FIG. 2b, does not include edge aberrations similar to those of test workpiece 127, as shown in FIG. 2a. In actuality, reference workpiece 126 also has edge aberrations but these have been purposely removed from FIG. 2b so that the edge aberration avoidance criteria are more easily understood.

With an understanding that both workpieces 126 and 127 generally have edge aberrations and that the aberrations are not in corresponding locations, it will be appreciated that as beams 119 and 122 scan over the edges of workpieces 126 and 127, when located at a nominal reference position, the intensity modulation imparted to beams 119 and 122 will differ due to these pattern differences. To further define the effects of these pattern differences, normalized relative responses of the photodetected modulated signals, denoted as $P_{131}$ and $P_{132}$, are plotted as a function of spot and edge location about a nominal point in FIG. 3.

Figure 3:
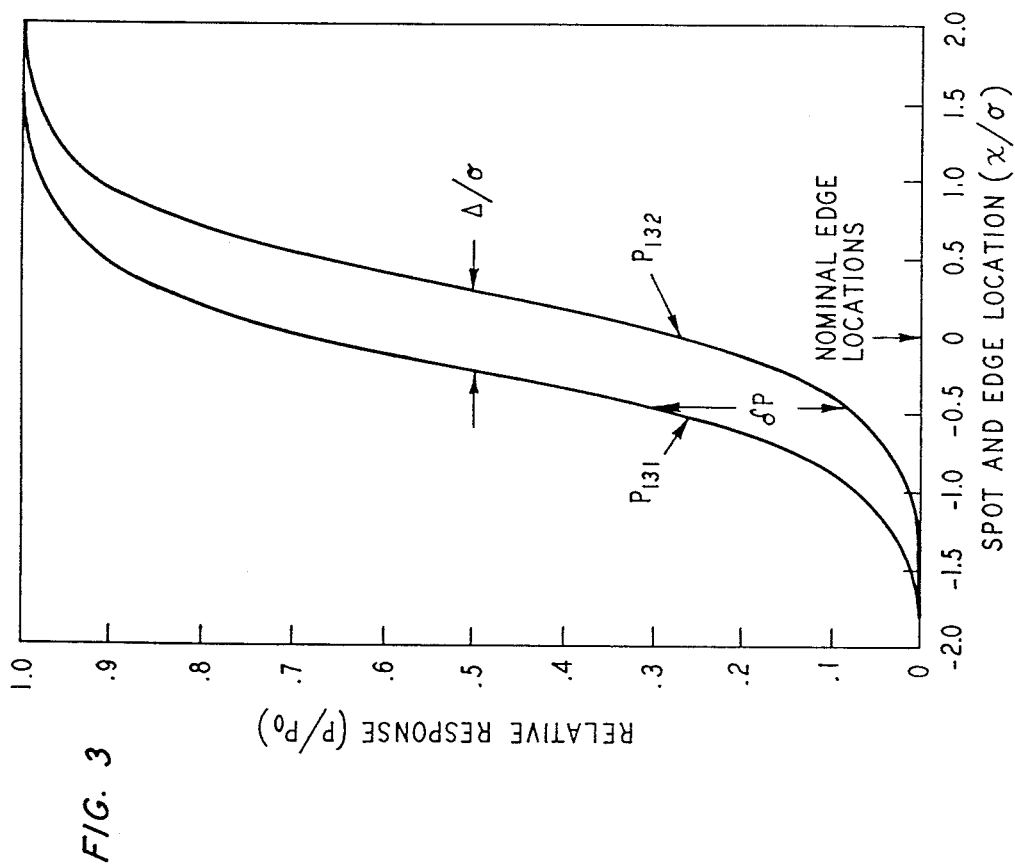
FIG. 3 is a plot of the relative photo responses of two scanning light beams as a function of light spot and pattern edge location.

Spot and edge location $x/\sigma$ is plotted along the abscissa with the nominal reference position or edge location represented as the point labeled O. The parameter $\sigma$ in FIG. 3 represents the spot size of beams 119 and 122 at the plane containing workpieces 126 and 127. $x$ is a variable representing the location of the spot about the nominal reference position.

$\Delta$ corresponds to the tolerance zone noted previously and represents the maximum tolerable deviation between a pattern edge on reference workpiece 126 and a corresponding pattern edge on test workpiece 127 at an equivalent position. Accordingly, $\Delta/\sigma$ represents the maximum allowable normalized deviation between edge locations of equivalent points on the patterns of workpieces 126 and 127.

Relative response is the ordinate parameter of FIG. 3 and is developed by normalizing the output signals from photodiodes 131 and 132 by division by reference power $P_o$. $P_o$ is the maximum signal power detected by photodiodes 131 and 132 when beams 119 and 122 are incident on a nonopaque portion of workpieces 126 and 127.

For the case where the edges of workpieces 126 and 127 are in correspondingly equivalent positions at the nominal edge location O, the $P_{131}$ curve will fall on top of the $P_{132}$ curve and both curves will have a normalized relative response which passes through the one-half relative response point. As either or both of the edge locations of workpieces 126 and 127 deviate in a nonidentical way about the nominal edge location O, the $P_{131}$ curve and the $P_{132}$ curve no longer fall atop one another. Ascribing one-half the maximum allowable edge deviation from the nominal location to reference workpiece 126 and one-half to test workpiece 127 in oppositely directed senses results in the plot shown in FIG. 3. It will be appreciated that although the $P_{132}$ curve is shown to the right of the $P_{131}$ curve and could, in effect, be considered as leading the $P_{131}$ curve, that is, beam 122 approaches an edge on test workpiece 127 before beam 119 reaches a corresponding edge point on reference workpiece 126, the inverse situation is equally probable. That is, beam 119 is just as likely to reach an edge point on reference workpiece 126 before beam 122 reaches a corresponding edge point on test workpiece 127. The significance to be attached to this effect will become evident in the discussion of FIG. 4.

To complete the discussion of FIG. 3 it should be noted that the vertical separation, δP, between the $P_{131}$ curve and the $P_{132}$ curve, represents the relative power difference between the two signals delivered by photodiodes 131 and 132 and that this power difference results from differences in the intensity modulation imparted to beams 119 and 122 as they are transmitted through workpieces 126 and 127. These modulation differences are produced by either acceptable edge aberrations, including mechanical misalignments, or by unacceptable pattern defects in the pattern being inspected.

Figure 4:
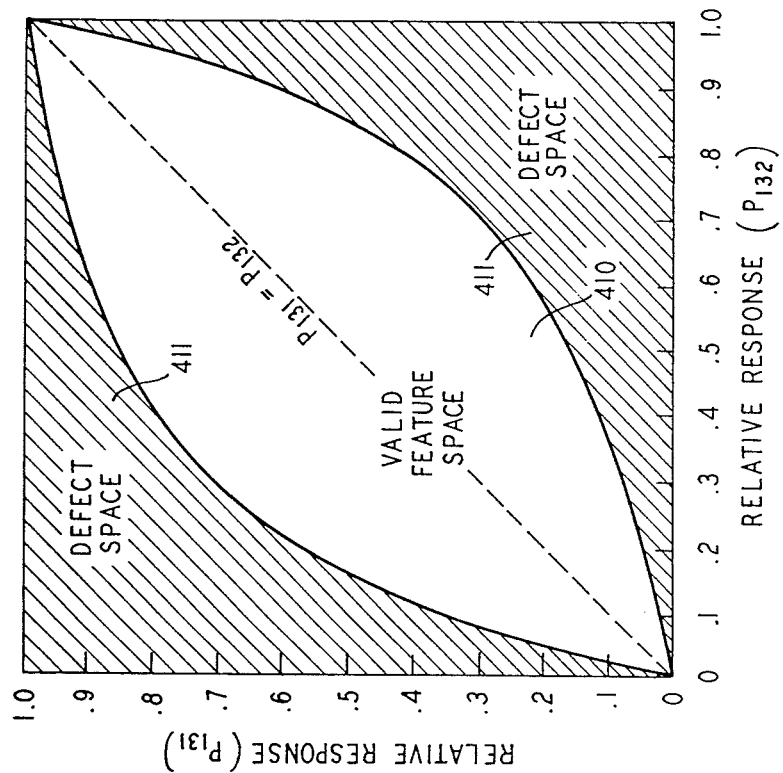
FIG. 4 is a plot of the relative photo responses (such as those of FIG. 3) of two light beams independent of their positional locations, illustrating valid feature space, including acceptable edge aberrations, and a defect space resulting from unacceptable pattern variations on the test workpiece.

In FIG. 4, the positional parameters of FIG. 3 are eliminated by plotting the relative responses $P_{131}$ and $P_{132}$ as a function of one another. For example, for any given normalized spot and edge location $x/\sigma$ there is a relative response power level for $P_{131}$ and a relative response power level for $P_{132}$. These two power levels, when plotted against one another, form one of the bounding curves of a football-shaped space 410 in FIG. 4. It should be recalled that the probability of either beam 119 or beam 122 first striking an edge is equally likely so that $P_{131}$ and $P_{132}$ are readily interchangeable in FIG. 3. Consequently, the other bounding curve of the football-shaped space 410 is produced as a result of such an interchange.

With the edge deviation Δ at the maximum allowable limit, all of the area contained within the football-shaped space 410 represents valid feature space including acceptable edge aberrations. All of the area external to the football-shaped space 410 represents a defect space 411 and includes all unacceptable pattern variations. Hence, the bounding curves represent a threshold level whereby acceptable pattern defects, including edge aberrations and mechanical misalignments are separable from unacceptable pattern defects.

3. Multiple Threshold Gating

Figure 5:
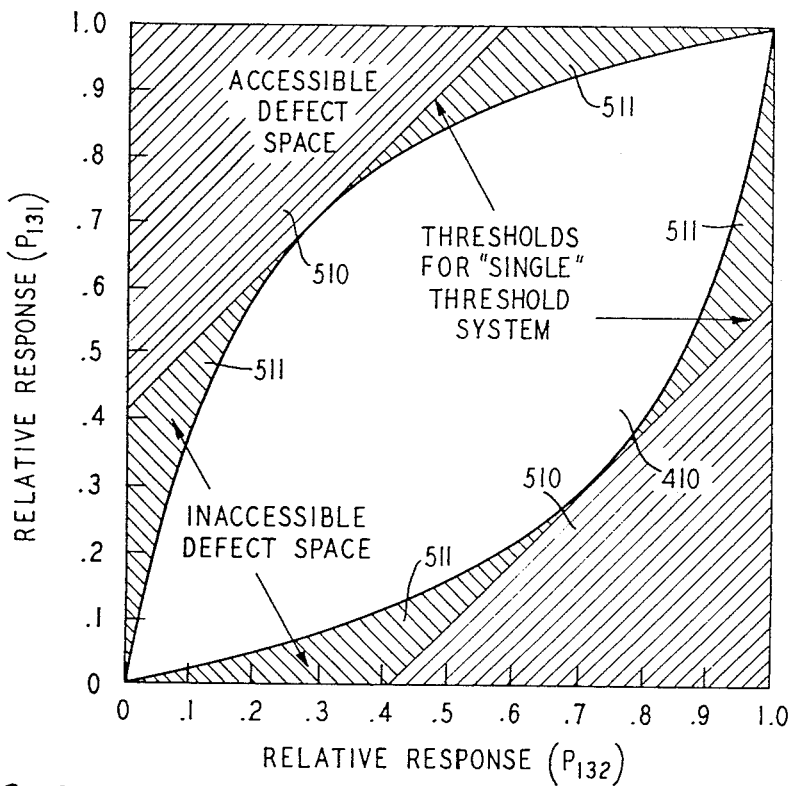
FIGS. 5 and 6 are defect space plots similar to that of FIG. 4 illustrating different degrees of resolution in results for single and multiple threshold system configurations.

Implementation of threshold gating which would accurately synthesize the nonlinear bounding curves of the football-shaped space 410 would optimize the edge aberration avoidance criteria. Such an implementation would involve the use of nonlinear, active circuit elements. For present applications, however, the synthesis of such a complex nonlinear shape is not necessary. As a first approximation to the nonlinear bounding curves a single threshold is employed. This threshold is represented as a straight line which is just tangent to the nonlinear curves, as shown in FIG. 5, at the point of maximum deviation from a straight line passing through the origin and the (1,1) relative response point. A system utilizing such a threshold provides capability for separating out those defects shown in shaded areas 510 of FIG. 5. However, a considerable portion of defect space 511 lying between the bounding curves and the tangential straight line approximation would be inaccessible. Unacceptable defects lying in this inaccessible area 511 would go undetected.

Figure 6:
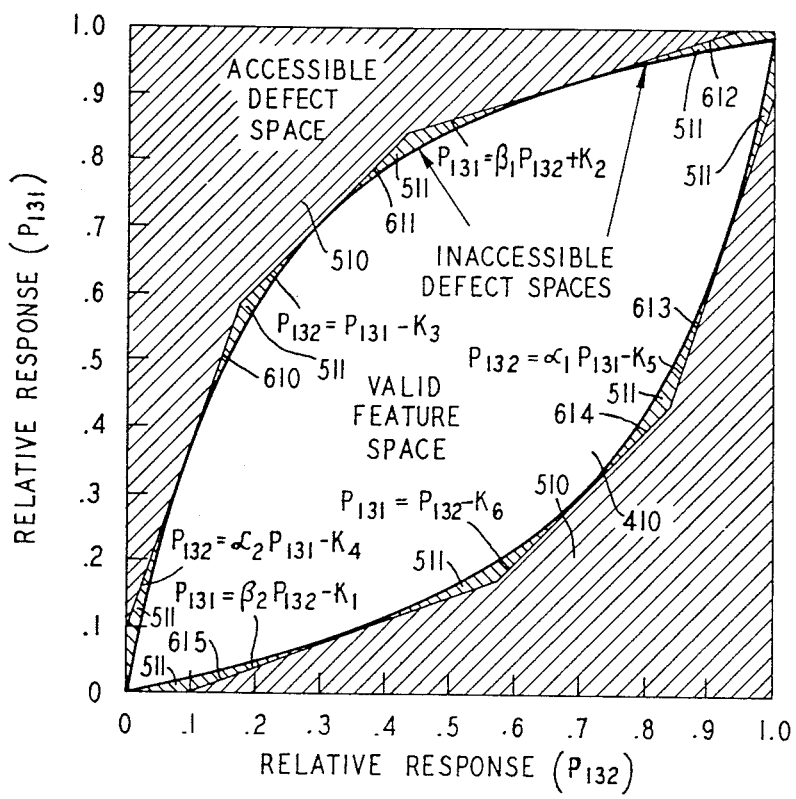

A reduction in this inaccessible defect space and hence, a corresponding improvement in sensitivity is effected by increasing the number of straight line segments bounding the nonlinear threshold curves. As shown in FIG. 6, for example, a three segment piecewise linear fit to one of the bounding threshold curves significantly reduces the inaccessible defect space 511. In fact, the points of tangency of line segments 610 through 615 are selected such that the inaccessible defect space 511 is minimized. It should be noted that the increased defect sensitivity is achieved without an increased sensitivity to edge aberrations and mechanical misalignments since tighter tolerances are not required on the mechanical alignment equipment.

Straight line segments 610 through 615 bounding the football-shaped space 410 are each definable by a slope parameter and an intercept parameter in the usual manner used to describe a straight line on a two-dimensional space. Translation of the line segments 610 through 615 into a form which may be implemented by logic circuitry results in defect region or space 510 being defined by the following conditions:

$$\alpha_2 P_{131} \geq P_{132} + K_4 \qquad (1)$$

$$P_{132} \leq P_{131} - K_3 \qquad (2)$$

$$\beta_1 P_{132} \leq P_{131} - K_2 \qquad (3)$$

$$\alpha_1 P_{131} \leq P_{132} + K_5 \qquad (4)$$

$$P_{131} \leq P_{132} - K_6 \qquad (5)$$

$$\beta_2 P_{132} \geq P_{131} + K_1 \qquad (6)$$

where $\alpha_1$, $\alpha_2$, $\beta_1$ and $\beta_2$ represent slope coefficients and $K_1$ through $K_6$ represent intercept coefficients.

It should be noted that line 610 is advantageously so chosen to be parallel to line 613. Also line 611 is made parallel to line 614 with both lines being parallel to line $P_{131} = P_{132}$ passing through the origin and the (1,1) relative response point. Accordingly, lines 611 and 614 have a unity slope coefficient. Finally, line 612 and line 615 are parallel to one another. These parallel relationships simplify fabrication of processing electronics 135 since $$\beta_1 = \beta_2, \qquad (7)$$

and $$\alpha_1 = \alpha_2. \qquad (8)$$

An inverse proportionality relationship between the α's and the β's results from the symmetrical orientation of lines 610 and 615 and lines 612 and 613 about the $P_{131} = P_{132}$ line. In one embodiment $$\beta_1 = \beta_2 = \frac{1}{\alpha_1} = \frac{1}{\alpha_2} = 0.3, \qquad (9)$$

and $$K_1 = 0.03$$

$$K_2 = 0.73$$

$$K_3 = 0.4$$
$$K_4 = 0.333$$
$$K_5 = 2$$
$$K_6 = 0.4 . \tag{10}$$

Figure 7:
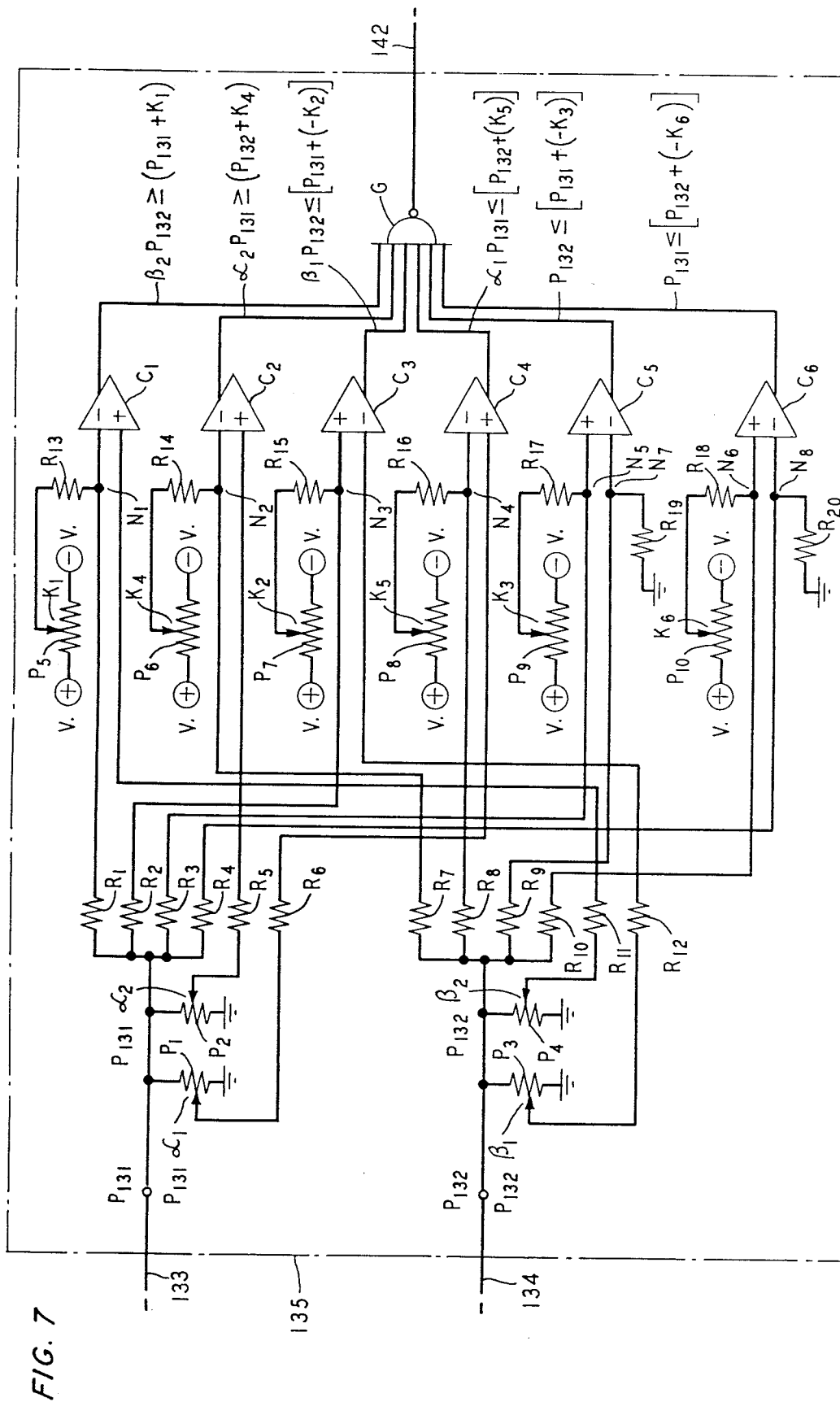
FIG. 7 is an electrical schematic representation of the processing electronics for realizing the multiple threshold resolution shown in FIG. 6.

FIG. 7 illustrates circuit implementation of conditions (1) through (6). Four of the six threshold conditions as set out in equations (1), (3), (4) and (6) require weighting of the first and second modulated signals $P_{131}$ and $P_{132}$, coupled out of photodiodes 131 and 132, respectively, by the slope coefficients ($\alpha$'s and $\beta$'s). The values of modulated signals $P_{131}$ and $P_{132}$ are referenced to ground potential. Signal weighting is effected electrically by applying $P_{131}$ to one side of parallel connected potentiometers $P_1$ and $P_2$ and by applying $P_{132}$ to one side of parallel connected potentiometers $P_3$ and $P_4$. The other side of potentiometers $P_1$ through $P_4$ is held fixed at a reference ground potential. Since a linear weighting is effected by potentiometers $P_1$ through $P_4$, only the ratio ($\alpha$'s and $\beta$'s) of wiper settings to full scale settings is important and specific resistance values need not be defined.

Intercept coefficient signals $K_1$ through $K_6$ are provided by a bipolar biasing arrangement of potentiometers $P_5$ through $P_{10}$. Each of the potentiometers $P_5$ through $P_{10}$ has one side connected to a source of positive potential +V and the other side connected to a source of negative potential −V. This bipolar biasing arrangement permits control of both the magnitude and the sign of the intercept coefficients. It should be noted that the signal values at the wipers of potentiometers $P_5$ through $P_{10}$ represent the intercept values directly. Both the positive and the negative sources of potential should have a low internal impedance to avoid any circuit loading effects.

$P_{131}$ and $P_{132}$, their product with the slope coefficients at the potentiometer wipers, and the intercepts at the potentiometer wipers are combined at inputs to comparators $C_1$ through $C_6$ to form binary signals representing the six previously described conditions on inputs to a coincidence gate G. The sums are effected at circuit nodes $N_1$ through $N_6$ on upper inputs and the products and $P_{131}$ and $P_{132}$ are delivered to lower inputs of comparators $C_1$ through $C_6$.

In order for the summation of slope coefficient weighted signals and intercept coefficient signals to be effected accurately, any signal imbalances caused by resistive mismatches in the two signal paths to be summed must be avoided. For example, to obtain an accurate summation of two voltages the two path resistance values should be equal. Similarly, comparisons between signals are only meaningful if the signals are not affected by resistive mismatches. To avoid resistive mismatches, the summation of the slope voltage coefficient signals and the intercept coefficient signals is controlled by in-line, serially connected, resistors $R_1$, $R_2$, $R_3$, $R_7$, $R_8$, $R_{10}$ and $R_{13}$ through $R_{18}$. Corresponding control, to permit accurate comparisons being made by comparators $C_1$ through $C_6$, is provided by resistors $R_4$, $R_5$, $R_6$, $R_9$. $R_{11}$, $R_{12}$, $R_{19}$, and $R_{20}$. So long as these resistors have a value which is an order of magnitude or more greater than the resistance values of potentiometers $P_1$ throuogh $P_{10}$, the effects of the potentiometers on the summations or comparisons is negated. Since conditions (2) and (5) have slope coefficients of unity, $R_{19}$ and $R_{20}$ on the lower inputs of $C_5$ and $C_6$ serve a similar function as $P_1$ through $P_4$ on the lower inputs of $C_1$ through $C_4$. Proper signal summations for the purpose of accurately synthesizing equations 1 through 6 are ensured provided the following resistor relationships are maintained.

$$R_1 = R_{13}$$
$$R_2 = R_{15}$$
$$R_3 = R_{17}$$
$$R_4 = R_{20}$$
$$R_7 = R_{14}$$
$$R_8 = R_{16}$$
$$R_9 = R_{19}$$
$$R_{10} = R_{18}. \tag{11}$$

Resistors $R_1$ through $R_{20}$ need not have any particular values so long as the order of magnitude difference between resistor values and potentiometer values is maintained and the aforementioned resistor relationships are satisfied. In one embodiment $R_1$ through $R_{20}$ were equal in value with that value being about an order of magnitude larger than a common value of potentiometer resistance which was advantageously 500 ohms.

A binary indication of the presence of absence of an unacceptable pattern defect is provided by actuation of comparators $C_1$ through $C_6$ and NAND gate G. Comparators $C_1$ through $C_6$ have an inverting and a noninverting input and are functionally parallel in the circuit such that in the absence of an unacceptable defect the noninverting input of each comparator controls and a logical 1 is delivered at each comparator output. Detection of an unacceptable defect in test workpiece 127 causes a threshold to be exceeded and comparator control shifts to an inverting input on at least one of the comparators $C_1$ through $C_6$ and a logical 0 is delivered on its output. One or more logical 0's provided by comparators $C_1$ through $C_6$ as inputs to NAND gate G causes the output to go high or to a logical 1 state and the occurrence of this condition indicates the presence of an unacceptable defect.

The gate G output on lead 142 is a train of pulse or no-pulse times which are synchronous with the scan of beams 119 and 122 and with the horizontal and vertical deflection of oscilloscope 136. Each pulse on lead 142 produces a spot on oscilloscope 136 at a position corresponding to the position of the defect on test workpiece 127. The long persistence time feature of the storage oscilloscope 136 permits the results of a complete inspection to be displayed simultaneously thereby allowing an operator to mark the location of the defects on the test workpiece 127 for detailed visual inspection and repair purposes.

While the foregoing embodiment has been described in terms of a six threshold approximation, it will be appreciated that the number of approximating thresholds may be readily increased and that, in the limit, the nonlinear threshold curves bounding the football-shaped space 410 may be synthesized directly.

In all cases it is understood that the above described embodiment is illustrative of but a small number of the many possible specific embodiments which can represent applications of the principles of the invention.

Thus, numerous and varied other embodiments can readily be devised in accordance with these principles by those skilled in the art without departing from the spirit and scope of the invention.

What is claimed is:

1. Apparatus for comparing a light affecting, patterned workpiece with a similar reference workpiece to detect unacceptable defects in the patterned workpiece to the exclusion of acceptable edge aberrations, the apparatus comprising
   means for generating first and second synchronously scanning light signals,
   means for maintaining said workpieces in optically equivalent positions, said position maintaining means being movable in a plane orthogonal to said scanning light signals,
   means for detecting said light signals affected by said workpieces, said signals being intensity modulated by the patterns on said workpieces, and
   means for gating preselected combinations of said first and second modulated signals in accordance with a number of predetermined threshold levels to produce a binary signal indicative of said unacceptable defects in said patterned workpiece with respect to said reference workpiece to the exclusion of said acceptable edge aberrations.

2. The apparatus in accordance with claim 1 wherein the first and second light signals comprise
   collimated light beams, each beam having an intensity profile, as a function of diametric beam cross section in parallel planes containing said workpieces, which approximates a gaussian distribution.

3. The apparatus in accordance with claim 1 wherein the light signal generating means includes
   a light source providing a coherent output light beam,
   means for deflecting said beam in a plane orthogonal to a parallel plane containing at least one of said workpieces,
   means for focusing said beam, said focused beam having a diameter at said workpieces which is the same order of magnitude as the smallest defect to be detected, and
   means for dividing said focused beam into first and second components, said first component illuminating said patterned workpiece and said second component illuminating said reference workpiece.

4. The apparatus in accordance with claim 3 wherein the light source comprises
   a helium-neon laser having an operating wavelength of 6328 Angstroms.

5. The apparatus in accordance with claim 3 wherein the beam deflection means includes
   a mirror, means for oscillating said mirror about an axis parallel to one of said planes containing one of said workpieces and located in a back focal plane and passing through a focal point of said focusing means, and
   means for directing said light beam from said source to a point of incidence at said axis of oscillation of said mirror.

6. The apparatus in accordance with claim 3 wherein the focusing means comprises
   a lens for maintaining an axis of symmetry of said light beam orthogonal to said workpieces throughout a scan.

7. The apparatus in accordance with claim 3 wherein the beam division means includes
   a beam splitter which produces a first and a second output beam, said second beam being orthogonal to said first beam, and
   a mirror for redirecting said second beam in a direction parallel with said first beam, said beams being adjusted to be incident normally on said workpieces.

8. The apparatus in accordance with claim 3 further including
   means for indicating the number and location of said detected defects on said patterned workpiece.

9. The apparatus in accordance with claim 8 wherein the defect indicating means comprises
   a storage oscilloscope having
      a horizontal deflection input for controlling an $x$-axis defect location in a positional display,
      a vertical deflection input for controlling a $y$-axis defect location in said positional display, and
      an intensity modulation input for affecting a binary control signal indicating said detected defects in said display.

10. The apparatus in accordance with claim 9 wherein the position maintaining means comprises
    a traverse table providing an output signal proportional to position along its axis of travel, and
    means for coupling said positional signal to said horizontal deflection input of said storage oscilloscope to provide said $y$-axis defect location.

11. The apparatus in accordance with claim 9 wherein the beam deflection means includes
    a mirror means for oscillating said mirror about an axis parallel to one of said planes containing one of said workpieces and located in a back focal plane and passing through a focal point of said focusing means, and
    means for directing said light beam from said source to a point of incidence at said axis of oscillation of said mirror.

12. The apparatus in accordance with claim 11 wherein the mirror oscillating means includes
    a galvanometer oscillator mechanically coupled to said mirror, said oscillator providing an output signal proportional to scan position, and
    means for coupling said scan positional signal to said vertical deflection input of said storage oscilloscope to provide said $x$-axis defect location.

13. The apparatus in accordance with claim 1 wherein the light signal detecting means includes
    first and second photodiodes fixedly mounted independently of said position maintaining means, and
    means for coupling output signals from said photodiodes to said gating means.

14. The apparatus in accordance with claim 1 wherein the gating means includes
    means for differently weighting each of said modulated signals in accordance with a first criteria for producing first and second sets of slope coefficient weighted signals proportional to said first and second modulated signals, respectively,
    means for supplying a plurality of intercept coefficient signals in accordance with a second criteria, and
    means for fixing said first and second criteria by combining selected ones of said slope coefficient weighted signals with selected ones of said intercept coefficient signals to define approximately a region of acceptable modulation differences on a plot of normalized power responses of said first and second modulated signals against one another for different levels of deviation from equal modulation.

15. The apparatus in accordance with claim 14 wherein the gating means further includes
means for combining said first modulated signal with first selected ones of said intercept coefficient signals to produce a first set of sum signals,
means for combining said second modulated signal with second selected ones of said intercept coefficient signals to produce a second set of sum signals,
separate means for comparing specified sum signals of said first sum signal set with specified ones of said slope coefficient weighted signals of said second set and specified sum signals of said second sum signal set with specified ones of said slope coefficient weighted signals of said first set, to produce for each signal pair compared a binary indicator of the relative magnitude of signals of such signal pair, and
means for detecting coincident attainment of a predetermined combination of binary signal states of said indicators.

16. The apparatus in accordance with claim 14 wherein the weighting means for producing the first and second sets of slope coefficient signals includes
potentiometers for providing output signals controllable over a range between said modulated signals and a reference ground potential.

17. The apparatus in accordance with claim 14 wherein the means for supplying the plurality of intercept coefficient signals includes
potentiometers for providing output signals controllable over a range between a predetermined positive potential and a predetermined negative potential.

18. The apparatus in accordance with claim 14 wherein
all of said slope coefficient signals of said first set are equal in value,
all of said slope coefficient signals of said second set are equal in value, and
said first and second sets of slope coefficient signals are reciprocally related to one another.

19. The apparatus in accordance with claim 18 wherein
said first set of slope coefficient signals and said reciprocal value of said second set of slope coefficient signals are equal to 0.3.

20. The apparatus in accordance with claim 14 wherein
said plurality of intercept coefficient signals, designated as $K_1$ through $K_6$, inclusively, have values of 0.03, 0.73, 0.4, 0.333, 2 and 0.4, respectively.

21. Apparatus for comparing a light affecting, patterned workpiece with a similar reference workpiece to detect unacceptable defects in the patterned workpiece to the exclusion of acceptable edge aberrations, the apparatus comprising:
means for generating first and second synchronously scanning light signals;
means for maintaining said workpieces in optically equivalent positions, said position maintaining means being movable in a plane orthogonal to said scanning light signals;
means for detecting said light signals affected by said workpieces, said signals being intensity modulated by the patterns on said workpieces; and
gating means, including means for producing a first set of amplitude weighted replicas of said first and second modulated signals and means for generating a second set of predetermined, defect defining threshold levels, said gating means producing an output indication when at least one of said amplitude weighted replicas of said first and second modulated signals in said first set exceeds a corresponding defect defining threshold level in said second set thereby enabling the separation of unacceptable pattern defects to the exclusion of acceptable edge aberrations.

22. The apparatus in accordance with claim 21 wherein the correspondence between said amplitude weighted replicas of said first set and said defect defining thresholds of said second set is fixed by means for synthesizing a piecewise linear approximation enclosing a region of acceptable modulation differences on a plot of normalized power responses of said first and second modulated signals against one another for different levels of deviation from equal modulation.

* * * * *